US010765330B2

(12) United States Patent
Takeuchi

(10) Patent No.: US 10,765,330 B2
(45) Date of Patent: Sep. 8, 2020

(54) PROBE FOR PULSE PHOTOMETRY

(71) Applicant: NIHON KOHDEN CORPORATION, Shinjuku-ku (JP)

(72) Inventor: Masahiro Takeuchi, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 240 days.

(21) Appl. No.: 15/432,427

(22) Filed: Feb. 14, 2017

(65) Prior Publication Data

US 2017/0245770 A1     Aug. 31, 2017

(30) Foreign Application Priority Data

Feb. 29, 2016  (JP) ................. 2016-037054

(51) Int. Cl.
*A61B 5/024* (2006.01)
*A61B 5/1455* (2006.01)
*A61B 5/00* (2006.01)

(52) U.S. Cl.
CPC ...... *A61B 5/02427* (2013.01); *A61B 5/14551* (2013.01); *A61B 5/14552* (2013.01); *A61B 5/6826* (2013.01); *A61B 5/6844* (2013.01); *A61B 5/6832* (2013.01); *A61B 2562/0238* (2013.01); *A61B 2562/146* (2013.01); *A61B 2562/185* (2013.01)

(58) Field of Classification Search
CPC .................................................. A61B 5/02427
See application file for complete search history.

(56) References Cited

U.S. PATENT DOCUMENTS

| 4,865,038 A | 9/1989 | Rich et al. |
| 4,974,591 A * | 12/1990 | Awazu ............... A61B 5/02427 600/344 |
| 5,313,940 A * | 5/1994 | Fuse .................. A61B 5/02416 600/310 |
| 5,520,177 A | 5/1996 | Ogawa et al. |
| 5,638,818 A | 6/1997 | Diab et al. |
| 5,645,440 A | 7/1997 | Tobler et al. |

(Continued)

FOREIGN PATENT DOCUMENTS

| JP | S61-162934 A | 7/1986 |
| JP | H04-279145 A | 10/1992 |

(Continued)

OTHER PUBLICATIONS

"Thermal conductivity of Metals, Metallic Elements, and Alloys," The Engineering Toolbox, https://www.engineeringtoolbox.com/thermal-conductivity-metals-d_858.html, accessed Sep. 11, 2019. (Year: 2019).*

(Continued)

*Primary Examiner* — Michael W Kahelin
(74) *Attorney, Agent, or Firm* — Pearne & Gordon LLP

(57) ABSTRACT

A pulse photometry probe includes a holding member that includes a contact face which is to be in contact with living tissue of a patient, an emitter that is placed in the holding member, a detector that is placed in the holding member and detects light emitted from the emitter, and, a spacer that is disposed between the contact face and the emitter and has an opening, wherein an air layer defined by the opening is disposed between an emitting face of the emitter and the contact face.

12 Claims, 4 Drawing Sheets

(56) References Cited

U.S. PATENT DOCUMENTS

| | | | |
|---|---|---|---|
| 5,782,757 A * | 7/1998 | Diab | A61B 5/02427 356/41 |
| 5,934,925 A | 8/1999 | Tobler et al. | |
| 5,995,855 A | 11/1999 | Kiani et al. | |
| 6,088,607 A | 7/2000 | Diab et al. | |
| 6,256,523 B1 | 7/2001 | Diab et al. | |
| 6,280,213 B1 | 8/2001 | Tobler et al. | |
| 6,349,228 B1 | 2/2002 | Kiani et al. | |
| 6,356,774 B1 | 3/2002 | Bernstein et al. | |
| 6,546,267 B1 | 4/2003 | Sugiura et al. | |
| 6,580,086 B1 | 6/2003 | Schulz et al. | |
| 6,694,160 B2 | 2/2004 | Chin | |
| 2001/0009265 A1 | 7/2001 | Schulz et al. | |
| 2001/0045509 A1 | 11/2001 | Al-Ali | |
| 2001/0045532 A1 | 11/2001 | Schulz et al. | |
| 2002/0026107 A1 | 2/2002 | Kiani et al. | |
| 2002/0026109 A1 | 2/2002 | Diab et al. | |
| 2003/0045785 A1 | 3/2003 | Diab et al. | |
| 2003/0111592 A1 | 6/2003 | Al-Ali | |
| 2003/0162414 A1 | 8/2003 | Schulz et al. | |
| 2004/0147823 A1 | 7/2004 | Kiani et al. | |
| 2005/0043600 A1 | 2/2005 | Diab et al. | |
| 2005/0143631 A1 | 6/2005 | Al-Ali | |
| 2006/0097135 A1 | 5/2006 | Al-Ali | |
| 2006/0189859 A1 | 8/2006 | Kiani et al. | |
| 2007/0027376 A1 | 2/2007 | Todokoro et al. | |
| 2007/0038041 A1 * | 2/2007 | Yang | A61B 5/14535 600/310 |
| 2007/0156034 A1 | 7/2007 | Al-Ali | |
| 2009/0143657 A1 | 6/2009 | Diab et al. | |
| 2009/0318819 A1 | 12/2009 | Takeuchi et al. | |
| 2010/0123897 A1 | 5/2010 | Yang et al. | |
| 2011/0152645 A1 | 6/2011 | Kiani et al. | |
| 2011/0172942 A1 | 7/2011 | Al-Ali | |
| 2011/0264411 A1 | 10/2011 | Yang et al. | |
| 2012/0123278 A1 | 5/2012 | Diab et al. | |
| 2012/0238847 A1 | 9/2012 | Murozono et al. | |
| 2015/0131098 A1 | 5/2015 | Yang et al. | |

FOREIGN PATENT DOCUMENTS

| | | |
|---|---|---|
| JP | H06-505903 A | 7/1994 |
| JP | H06-327658 A | 11/1994 |
| JP | 2001-149349 A | 6/2001 |
| JP | 2002-525151 A | 8/2002 |
| JP | 2007-054594 A | 3/2007 |
| JP | 2008-099890 A | 5/2008 |
| JP | 2008-126017 A | 6/2008 |
| JP | 2008-539441 A | 11/2008 |
| JP | 2010-004928 A | 1/2010 |
| JP | 2012-191983 A | 10/2012 |
| WO | 92-16142 A1 | 10/1992 |

OTHER PUBLICATIONS

"Sapphire," Wikipedia, https://en.wikipedia.org/wiki/Sapphire, accessed Sep. 11, 2019. (Year: 2019).*

"Titanium," Wikipedia, https://en.wikipedia.org/wiki/Titaniunn, accessed Sep. 11, 2019. (Year: 2019).*

The engineering toolbox, "Thermal conductivity of common metals, metallic elements and Alloys," https://www.engineeringtoolbox.com/thermal-conductivity-metals-d_858.html. accessed Jan. 8, 2020 (Year: 2020).*

The engineering toolbox, "Thermal conductivity of some selected gases, insulation products, aluminum, asphalt, brass, copper, steel and other common materials," https://www.engineeringtoolbox.com/thermal-conductivity-d_429.html. accessed Jan. 8, 2020 (Year: 2020).*

Japanese Office action issued in Patent Application No. 2016-037054 dated Sep. 10, 2019.

Japanese Office action issued in Japanese Patent Application No. 2016-037054 dated Dec. 17, 2019.

* cited by examiner

PROBE FOR PULSE PHOTOMETRY

CROSS REFERENCE TO RELATED APPLICATION

This application is based on Japanese Patent Applications No. 2016-037054 filed on Feb. 29, 2016, the contents of which are incorporated herein by reference.

BACKGROUND

The present subject matter relates to a pulse photometry probe.

A pulse oximetry probe has been used which is to be wrapped around living tissue (for example, a finger of the hand, the back of the hand, or instep) of the patient, and which is capable of measuring vital sign information (for example, the arterial oxygen saturation (SpO2)) of the blood vessel of the living tissue.

For example, U.S. Pat. No. 6,694,160 discloses a tape-type pulse oximetry probe which is configured by a flexible transparent layer, a metal layer which is stacked on the transparent layer, emitting and detecting elements which are mounted on the metal layer, a white layer which is stacked on the metal layer, and an adhesive layer which is stacked on the white layer.

In the pulse oximetry probe disclosed in U.S. Pat. No. 6,694,160, however, the SpO2 is measured while the probe is wrapped around living tissue of the patient. In a state where the probe is wrapped around the living tissue of the patient, there is a possibility that heat generated from the emitting element may be concentrated in part of the finger through the adhesive layer, and the patient may be caused to feel a sense of discomfort.

In a pulse photometry probe such as a pulse oximetry probe, in order to improve the accuracy of measuring vital sign information which is obtained from the blood vessel of thick living tissue, it is requested to mount an emitting element which can emit high power light, in the probe. In the case where such an emitting element is mounted in the tape-type pulse oximeter disclosed in Patent Literature 1, heat generated from the emitting element may be concentrated in the part of the living tissue, and therefore the drawback due to heat generated from the emitting element may become remarkable.

The subject matter provides a pulse photometry probe in which heat generated from an emitting element can be prevented from being concentrically transmitted to part of living tissue of the patient.

SUMMARY

According to an aspect of the subject matter, a pulse photometry probe includes a holding member that includes a contact face which is to be in contact with living tissue of a patient, an emitter that is placed in the holding member, a detector that is placed in the holding member and detects light emitted from the emitter, and a spacer that is disposed between the contact face and the emitter and has an opening, wherein an air layer defined by the opening is disposed between an emitting face of the emitter and the contact face.

According to the subject matter, it is possible to provide a pulse photometry probe in which heat generated from an emitting element can be prevented from being concentrically transmitted to part of living tissue of the patient.

DETAILED DESCRIPTION OF EMBODIMENTS

Figure 1:
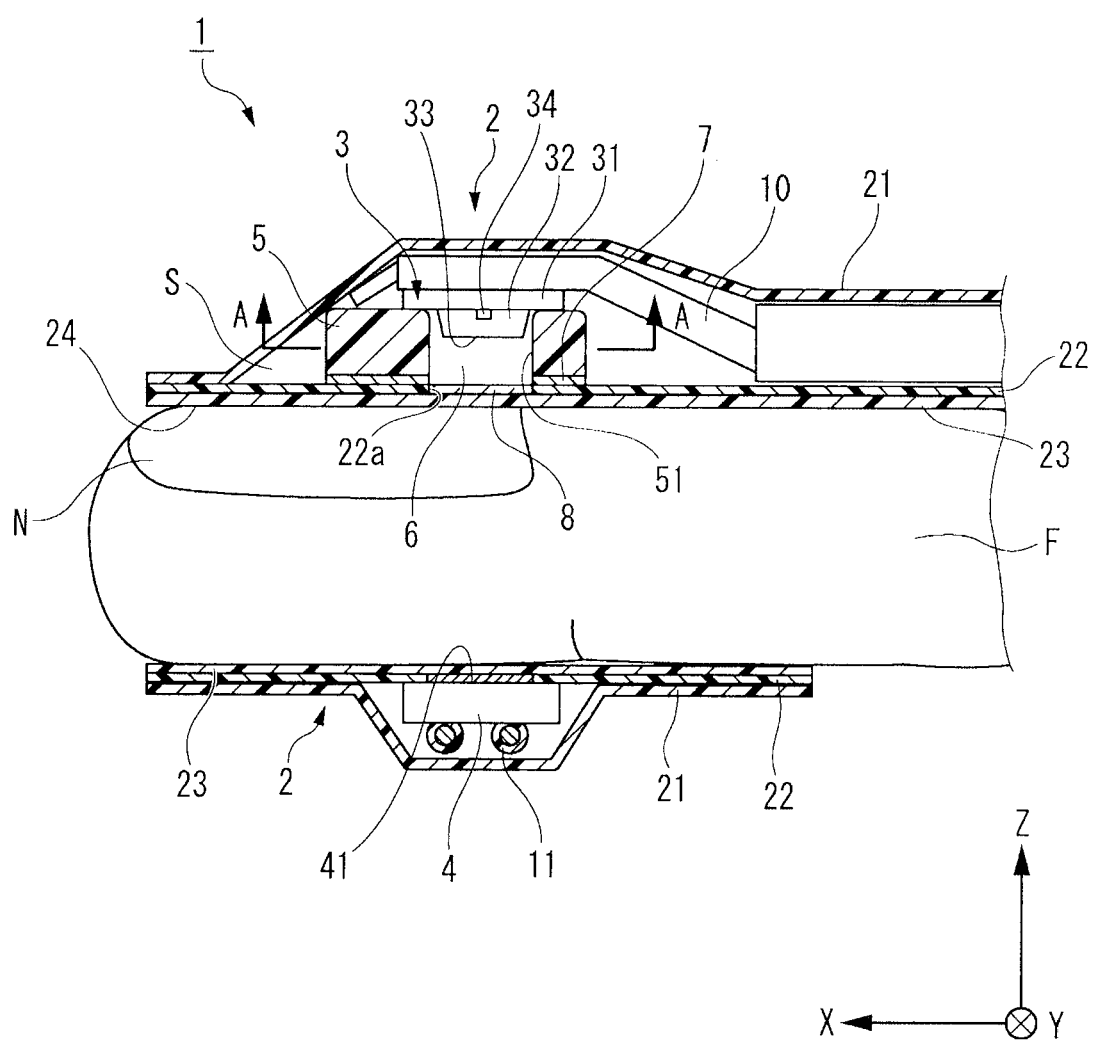
FIG. 1 is a sectional view illustrating a probe for pulse photometry of an embodiment of the subject matter.

Hereinafter, an embodiment of the subject matter will be described with reference to the drawings. In the description of the embodiment, description of components which are denoted by the same reference numerals as those designating components that have been already described will be omitted for the sake of convenience in description. The dimension ratios of components illustrated in the drawings may be sometimes different from the actual ratios for the sake of convenience in description.

In the description of the embodiment, for the sake of convenience in description, the X-, Y-, and Z-axis directions will be appropriately referred. These directions are relative directions which are set with respect to a pulse photometry probe 1 (hereinafter, referred to simply as the probe 1) illustrated in FIG. 1. Here, the X-axis direction includes the +X direction (the direction indicated by the arrow) and the −X direction, the Y-axis direction includes the +Y direction (the direction indicated by the arrow) and the −Y direction, and the Z-axis direction includes the +Z direction (the direction indicated by the arrow) and the −Z direction. The +Z direction is defined as the upward direction, and the −Z direction as the downward direction.

FIG. 1 is a sectional view illustrating the probe 1 of the embodiment. The probe 1 is wrapped around a finger F of the patient. The finger is living tissue. In FIG. 1, a sectional view of the probe 1 is illustrated, but, for the sake of convenience in description, the finger F is not illustrated as a sectional view, but illustrated as a side view. Alternatively, the probe 1 may be wrapped around a toe, or the back of the hand or instep of the patient in place of the finger F of the patient. The probe 1 is a pulse oximetry probe (disposable type) which, when the probe is wrapped around living tissue of the patient, for example, can measure the arterial oxygen saturation ($SpO_2$), or the like. The probe 1 may include a holding member 2, an emitter 3, a detector 4, a spacer 5, a heat radiation layer 7, and a transparent member 8.

The holding member 2 may include an upper sheet 21, a lower sheet 22, and an adhesive tape 23. The upper sheet 21 and the lower sheet 22 may be configured by the same material, and are configured by a flexible resin material or the like. The upper sheet 21 is joined to the lower sheet 22. An accommodation space S for accommodating components such as the emitter 3 and detector 4 which will be described later is formed by the upper sheet 21 and the lower sheet 22. The adhesive tape 23 is placed on the bottom face of the lower sheet 22, and to be contacted with the finger F of the patient during use of the probe 1. The adhesive tape 23 has a contact face 24 which is to be in contact with the finger F of the patient.

The emitter 3 is placed in the accommodation space S of the holding member 2, and may include a submount board 31, two emitting elements 34, and a lens 32 which covers the two emitting elements 34. The two emitting elements 34 are mounted on the submount board 31 in a state where the emitting elements are arranged in the Y-axis direction (see FIG. 3), but not limited to the arrangement. The two emitting elements 34 may be arranged in X-axis direction or Z-axis direction, or on an XY plane. When the probe 1 is to be used, as illustrated in FIG. 1, an emitting face 33 (corresponding to the surface of the lens 32) of the emitter 3 is preferably placed opposingly to the nail N of the finger F. For example, the emitting elements 34 are LEDs (Light Emitting Diodes). In the case where the probe 1 is a pulse oximetry probe, for example, one of the two emitting elements 34 is an LED which emits a red light beam, and the other of the two emitting elements 34 is an LED which emits an infrared light beam. The emitting elements 34 are driven by an electric signal supplied through a cable 10. The number of the emitting elements 34 is not particularly limited, and may be 1 or 3 or more. Also the emission wavelengths of the emitting elements 34 are not particularly limited.

The detector 4 is placed in the accommodation space S of the holding member 2. The detector 4 is configured so as to detect the light beams which are emitted from the emitting elements 34 of the emitter 3, and which are transmitted through the finger F, and has a detecting face 41. For example, the detector 4 is a PD (Photodiode). The number of the detector 4 is not particularly limited. In the case where the probe 1 is a pulse oximetry probe, for example, the detector 4 detects the red light beam emitted from the red LED, and the infrared light beam emitted from the infrared LED. An electric signal which is output from the detector 4 is supplied to a cable 11. In a state where the probe 1 has not yet been used (i.e., before the probe 1 is wrapped around the finger F), the emitter 3 and the detector 4 are juxtaposed in a predetermined direction (for example, the Y-axis direction).

Oxyhemoglobin contained in the blood which flows through the blood vessel in the finger F absorbs a larger amount of infrared light, and in contrast deoxyhemoglobin contained in the blood absorbs a larger amount of red light. When changes of the amounts of the red and infrared light beams which are emitted from the emitter 3, and which are transmitted through the finger F (particularly, the blood vessel in the finger F) are detected by the detector 4, therefore, it is possible to measure the SpO2.

Figure 3:
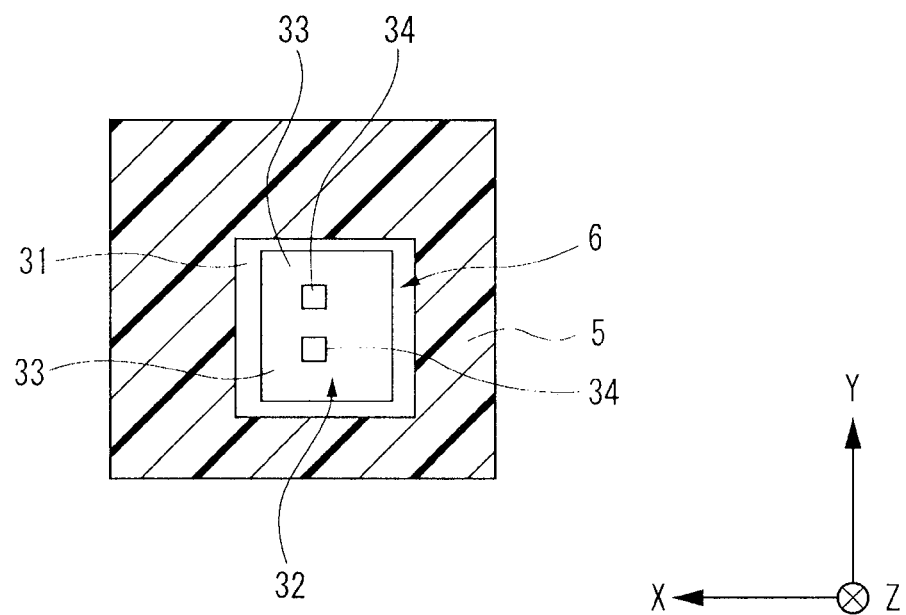
FIG. 3 is a sectional view of a spacer taken along A-A in FIG. 1.

The spacer 5 is placed in the Z-axis direction between the contact face 24 of the adhesive tape 23 and the submount board 31 of the emitter 3. The spacer 5 is in contact with the submount board 31, and formed by a resin material or the like. The spacer 5 has an opening 51 which passes through the spacer 5 in the thickness direction. As illustrated in FIG. 3, the emitting elements 34 are exposed through the opening 51. An air layer 6 which is defined by the opening 51 is disposed between the emitting face 33 of the emitter 3 and the contact face 24 of the adhesive tape 23 in the Z-axis direction.

The heat radiation layer 7 is disposed in the Z-axis direction between the spacer 5 and the contact face 24 of the adhesive tape 23. Particularly, the heat radiation layer 7 is formed on the bottom face of the spacer 5, and disposed in the Z-axis direction between the spacer 5 and the lower sheet 22. For example, the heat radiation layer 7 is formed by a metal material or a carbon material. The thermal conductivity of the heat radiation layer 7 is higher than that of the spacer 5.

The transparent member 8 is disposed in the Z-axis direction between the contact face 24 of the adhesive tape 23 and the emitter 3. Particularly, the transparent member 8 is placed opposingly to the emitting face 33 of the emitter 3, and disposed in a through hole 22a which is formed in the lower sheet 22. The transparent member 8 is configured so as to allow the light beams emitted from the emitting elements 34, to pass therethrough, and formed by transparent resin material which is harder than the holding member 2 (particularly, the lower sheet 22).

Figure 2:
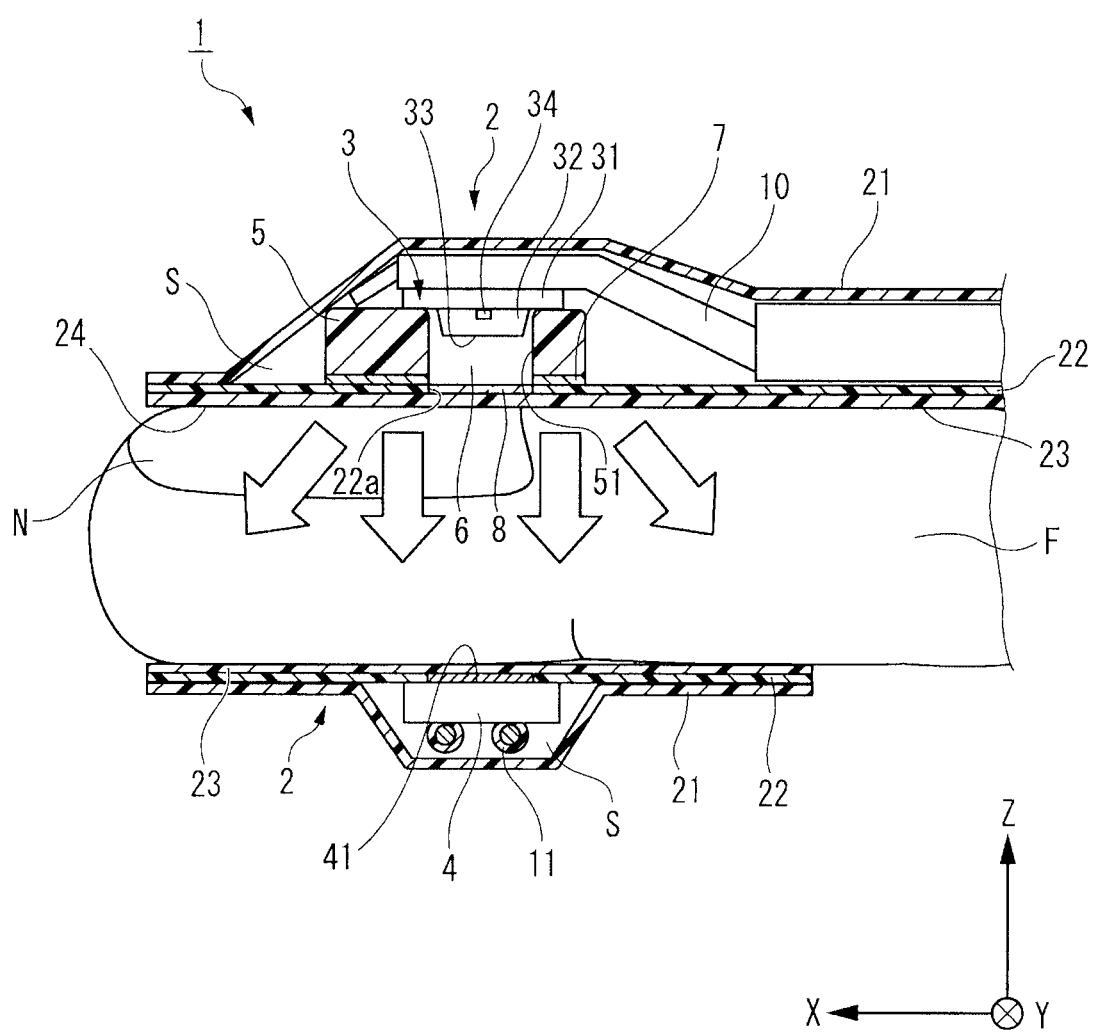
FIG. 2 is a diagram illustrating a manner in which heat generated from an emitter is transmitted to a finger of the patient.

Next, the manner in which heat generated from the emitting elements 34 is transmitted to the finger F of the patient will be described with reference to FIG. 2. FIG. 2 is a diagram schematically illustrating the manner in which heat generated from the emitting elements 34 is transmitted to the finger F. The arrows indicated in FIG. 2 diagrammatically show the manner of heat transmission. As illustrated in FIG. 2, during the period when the emitting elements 34 emit the light beams, most of heat generated at the emitting elements 34 is transmitted to the finger F through the submount board 31, the spacer 5, the heat radiation layer 7, the lower sheet 22, and the adhesive tape 23. By contrast, part of the heat generated at the emitting elements 34 is transmitted to the finger F through the air layer 6, the transparent member 8, and the adhesive tape 23. In this way, it is possible to prevent heat generated at the emitting elements 34 from being concentrically transmitted to a part of the finger F. In the case where an air layer is not disposed between the emitting face 33 of the emitter 3 and the adhesive tape 23 as in the prior art, particularly, most of heat generated from the emitting elements 34 is concentrated in the parts of the finger F which are opposed to the emitting elements 34, and therefore there is a possibility that the patient may suffer a low-temperature burn. According to the embodiment, by contrast, the sufficient air layer 6 is disposed between the emitting face 33 of the emitter 3 and the transparent member 8, and therefore most of heat generated from the emitting elements 34 is dispersedly transmitted through the spacer 5. As a result, the patient can be prevented from suffering a low-temperature burn.

According to the embodiment, moreover, the heat radiation layer 7 is disposed between the spacer 5 and the lower sheet 22. Therefore, heat generated from the emitting elements 34 can be transmitted more efficiently and dispersedly to the finger F.

In the case where the heat radiation layer 7 is formed by a metal material, moreover, part of the diverging light emitted from the emitting elements 34 is reflected by the heat radiation layer 7. In the case where the heat radiation layer 7 is formed by a carbon material (for example, carbon black), by contrast, part of the diverging light is absorbed by the heat radiation layer 7. In this way, in the case where the heat radiation layer 7 is formed by a metal material or a carbon material, only parallel light beams emitted from the emitting elements 34, and emission light with a small divergence angle are enabled to enter the detector 4. Therefore, the accuracy of measuring vital sign information such as the SpO2 can be improved.

Since the transparent member 8 is disposed between the adhesive tape 23 and the emitting elements 34, it is possible to prevent the distance between the emitting elements 34 and part of the finger F, from being reduced by entrance of the part of the finger F toward the air layer 6. Therefore, a phenomenon in which part of heat generated from the emitting elements 34 is concentrically transmitted to the part of the finger F entering toward the air layer 6 can be prevented from occurring.

Figure 4:
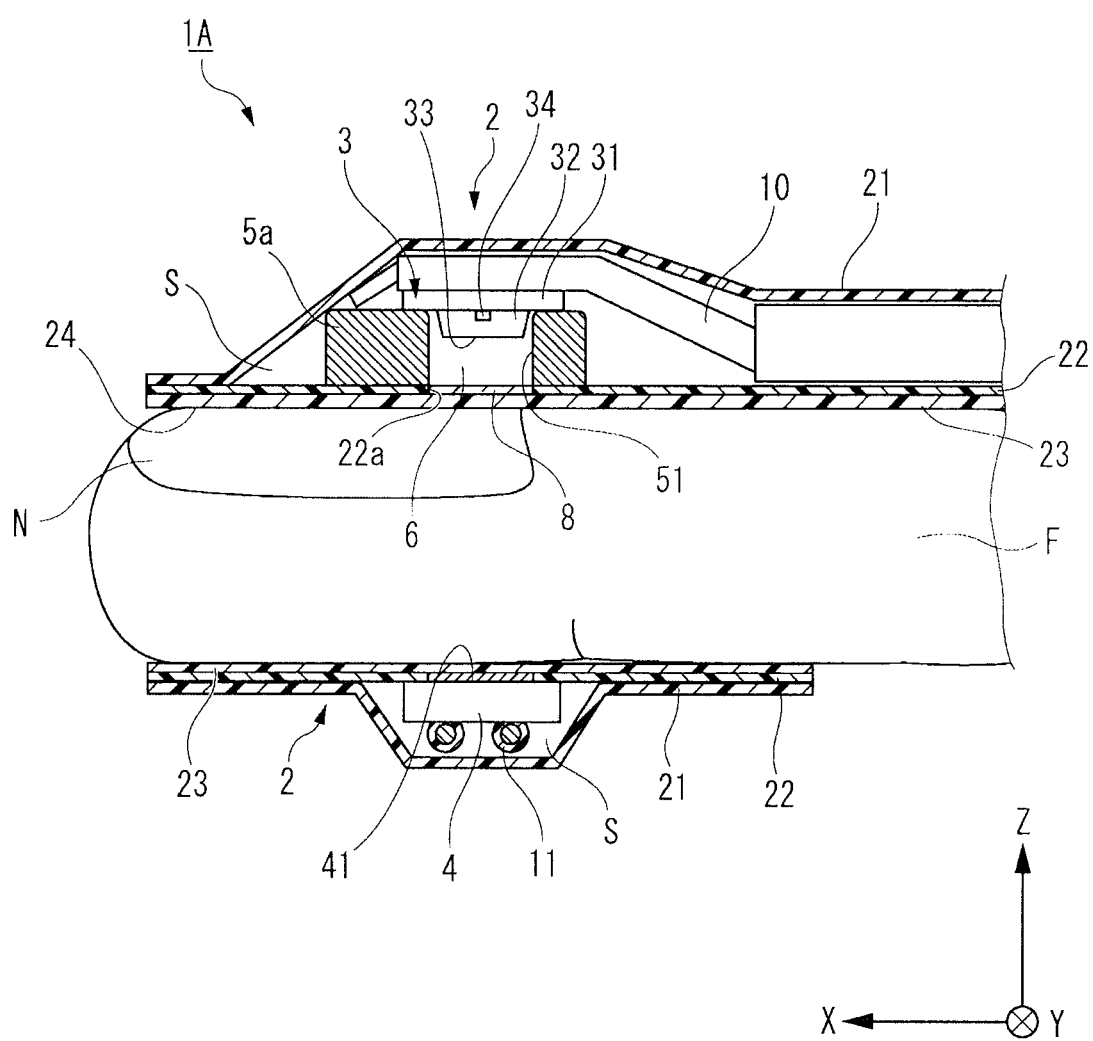
FIG. 4 is a sectional view illustrating a modification of the pulse photometry probe of the embodiment of the subject matter.

Next, a pulse photometry probe 1A (hereinafter, referred to simply as the probe 1A) of a modification of the embodiment will be described with reference to FIG. 4. FIG. 4 is a sectional view illustrating the probe 1A. As illustrated in FIG. 4, the probe 1A is different from the probe 1 illustrated in FIG. 1 in that the spacer 5 is replaced with a spacer 5a, and that the heat radiation layer 7 is not disposed. In the following description, only the spacer 5a will be described.

The spacer 5a is different from the spacer 5 in that the spacer 5a is formed by a metal material. Since the spacer 5a is formed by a metal material with high thermal conductivity, heat generated from the emitting elements 34 can be efficiently transmitted to the finger F even in the configuration where the heat radiation layer 7 is not disposed.

Although the embodiment of the subject matter has been described, the technical scope of the invention should not be restrictively interpreted based on the description of the embodiment. The embodiment is a mere example, and those skilled in the art will understand that the embodiment can be variously changed within the scope of the invention as defined by the appended claims. The technical scope of the invention should be determined with reference to the claims along with the full scope of equivalents.

What is claimed is:

1. A pulse photometry probe comprising:
   a holding member that includes a contact face which is to be in contact with living tissue of a patient and a lower sheet in which a through hole is formed;
   an emitter that is placed in the holding member;
   a detector that is placed in the holding member and detects light emitted from the emitter;
   a spacer that is disposed between the contact face and the emitter and has an opening;
   a transparent member that is disposed between the contact face and the emitter, covers the opening of the spacer, and is harder than the holding member; and
   a heat radiation layer that is disposed between the spacer and the lower sheet and has a thermal conductivity that is higher than a thermal conductivity of the spacer,
   wherein an air layer defined by the opening is disposed between an emitting face of the emitter and the contact face, and
   wherein the transparent member, emitter, detector, and opening of the spacer are aligned along a linear direction.

2. The probe according to claim 1 wherein the heat radiation layer is disposed between the spacer and the contact face.

3. The probe according to claim 2, wherein the heat radiation layer is formed by a metal material or a carbon material.

4. The probe according to claim 1, wherein the spacer is formed by a metal material.

5. The probe according to claim 1, wherein the holding member forms an accommodation space, and the emitter and the detector are accommodated in the accommodation space.

6. The probe according to claim 1, wherein the air layer is surrounded by the spacer, the emitting face and the transparent member.

7. The probe according to claim 1, wherein the lower sheet is disposed between the contact face and the spacer.

8. The probe according to claim 7, wherein a lower surface of the lower sheet and a lower surface of the transparent member form a continuous surface.

9. The probe according to claim 1, wherein:
   the holding member includes an upper sheet,
   the emitter and detector are place between the upper sheet and lower sheet of the holding member,
   the spacer is disposed in the holding member between the lower sheet and the emitter, and
   the air layer is disposed between the emitter and the transparent member.

10. The probe according to claim 1, wherein the transparent member, emitter, and opening of the spacer are aligned along a linear direction, and the transparent member has a rectangular cross-section along a plane parallel to the linear direction.

11. The probe according to claim 1, wherein the contact face covers the air layer.

12. A pulse photometry probe comprising:
    a holding member that includes a contact face which is to be in contact with a finger of a patient and a lower sheet in which a through hole is formed;
    an emitter that is placed in the holding member;
    a detector that is placed in the holding member and detects light emitted from the emitter;
    a spacer that is disposed between the contact face and the emitter and has an opening;
    a transparent member that is disposed between the contact face and the emitter, covers the opening of the spacer, and is harder than the holding member; and
    a heat radiation layer that is disposed between the spacer and the lower sheet and has a thermal conductivity that is higher than a thermal conductivity of the spacer,
    wherein an air layer defined by the opening is disposed between an emitting face of the emitter and the contact face, and
    wherein the air layer disperses most of the heat from the emitter to the spacer thereby preventing low temperature burns in the finger.

* * * * *